United States Patent [19]

Anderson et al.

[11] Patent Number: 5,670,456

[45] Date of Patent: Sep. 23, 1997

[54] COMPOUNDS

[75] Inventors: Richard J. Anderson; Joe T. Bamberg, both of Palo Alto; Michael M. Leippe, Boulder Creek, all of Calif.

[73] Assignee: Sandoz Ltd., Basel, Switzerland

[21] Appl. No.: 447,332

[22] Filed: May 22, 1995

Related U.S. Application Data

[63] Continuation of Ser. No. 225,037, Apr. 8, 1994, Pat. No. 5,506,191, which is a continuation of Ser. No. 26,247, Mar. 4, 1993, abandoned, which is a continuation of Ser. No. 718,719, Jun. 21, 1991, abandoned, which is a continuation-in-part of Ser. No. 492,527, Mar. 9, 1990, abandoned, which is a continuation of Ser. No. 115,288, Nov. 2, 1987, abandoned.

[51] Int. Cl.$^6$ .................. C07C 281/14; A01N 47/30

[52] U.S. Cl. .................. 504/280; 504/328; 504/343; 548/379.4; 558/8; 562/624; 564/36

[58] Field of Search ............... 564/36; 562/624; 558/8; 548/379.4; 504/328, 343, 280

[56] References Cited

FOREIGN PATENT DOCUMENTS 34010  8/1981  European Pat. Off. .

*Primary Examiner*—Robert Gerstl
*Attorney, Agent, or Firm*—Lynn Marcus-Wyner

[57] ABSTRACT

N-carbamoyl-2-carboxyaryl-heterocyclic and hydrazinecarboximidamidehydrazone derivatives, intermediates and processes for their preparation, agricultural compositions containing them and their use as agricultural chemicals, in particular herbicides.

12 Claims, No Drawings

COMPOUNDS

This is a continuation of application Ser. No. 08/225,037, filed on Apr. 8, 1994, now U.S. Pat. No. 5,506,191, which is a continuation of application Ser. No. 08/026,247, filed on Mar. 4, 1993, now abandoned, which is a continuation of application Ser. No. 07/718,719, filed on Jun. 21, 1991, now abandoned, which is a continuation-in-part of application Ser. No. 07/492,527, filed on Mar. 9, 1990, now abandoned, which is a continuation of application Ser. No. 07/115,288, filed on Nov. 2, 1987, now abandoned.

The present invention concerns N-carbamoyl-2-carboxyaryl-heterocyclic and hydrazinecarboximidamido-hydrazone derivatives, intermediates and processes for their preparation, agricultural compositions containing them and their use as agricultural chemicals, in particular herbicides.

More particularly the invention concerns compounds of the formula I

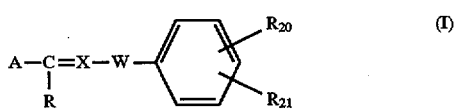

wherein W is

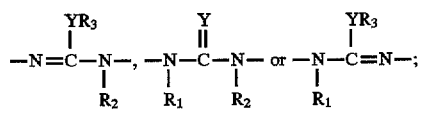

and a)
   R is hydrogen or alkyl;
   $R_1$ is hydrogen alkyl, alkoxyalkyl, hydroxyalkyl, aryl or substituted aryl or taken together with $R_3$ forms a 2 to 4 membered alkylene, alkenylene or mixed alkylenealkenylene bridge which may bear one or more substituents selected from halogen, alkyl, alkoxy, phenyl or substituted phenyl and in which any methylene may be replaced by a group selected from oxygen, sulfur $NR_{12}$, carbonyl or thiocarbonyl;
   X is N; and
   Y is $NR_4$; or b)
   R and $R_1$ taken together form a 2 to 4 membered alkylene, alkenylene or mixed alkylenealkenylene bridge which may bear one or more substituents selected from halogen, alkyl, alkoxy, phenyl or substituted phenyl and in which any methylene may be replaced by a group selected from oxygen, sulfur, $NR_{12}$, carbonyl or thiocarbonyl; wherein
   $R_{12}$ is hydrogen, alkyl, alkoxy, phenyl or substituted phenyl
   X is N or CH; and
   Y is O, S or $NR_4$; and
in each case A is the group

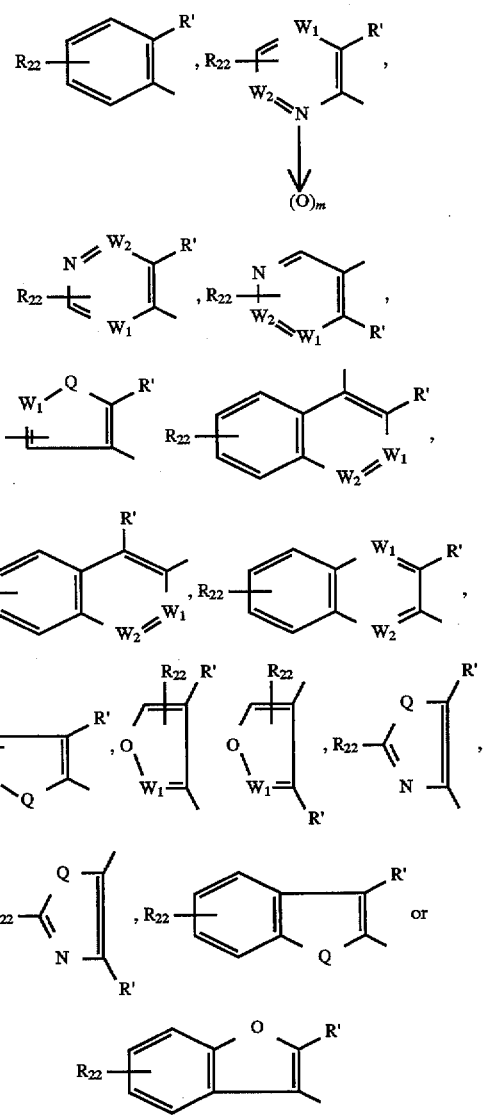

R' is a carboxyl group in free acid, salt or ester form, a thiocarboxyl group in free acid or ester form, a carbamoyl group or a mono- or di- substituted carbamoyl group;

each of $R_2$, $R_3$ and $R_4$ is independently hydrogen, alkyl, alkoxy, alkylamino, alkoxyalkyl, hydroxyalkyl, aryl or substituted aryl, or $R_3$ and $R_4$ taken together form a $C_3$–$C_6$ alkylene bridge optionally including one of oxygen, sulfur or N—$R_5$, or $R_3$ and $R_1$ taken together are as defined above, m is zero or one, Q is oxygen, sulfur or N—$R_5$, each of $W_1$ and $W_2$ is independently nitrogen or CH, $R_5$ is hydrogen or alkyl, and each of $R_{20}$, $R_{21}$ and $R_{22}$ is independently hydrogen, halogen, alkyl, alkenyl, alkynyl, alkoxy, alkenyloxy, alkynyloxy or alkylthio each optionally substituted by 1 to 6 halogen atoms; phenyl or phenoxy each optionally substituted; nitro, cyano, hydroxy, amino, alkylamino, dialkylamino, alkylcarbonyl or alkoxycarbonyl.

R' is preferably a carboxyl group in free acid, salt or ester form, COSR$_9$ or CONR$_7$R$_8$ especially COOR$_6$, COSR$_9$ or CONR$_7$R$_8$ wherein R$_6$ is hydrogen, alkyl, haloalkyl, alkoxyalkyl, phenyl, substituted phenyl, alkali or alkaline earth metal cation, ammonium cation, substituted ammonium cation, phosphonium cation, trialkyl sulfonium cation, trialkylsulfoxonium cation or the group

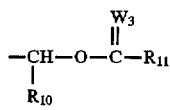

wherein each of R$_{10}$ and R$_{11}$ is independently hydrogen, alkyl or alkoxyalkyl and W$_3$ is oxygen or sulfur R$_9$ is alkyl, alkoxy, alkenyl, phenyl, substituted phenyl or benzyl each of R$_7$ and R$_8$ is independently hydrogen, alkyl, alkoxy, phenyl or substituted phenyl; or R$_7$ and R$_8$ taken together form a C$_3$–C$_6$ alkylene bridge optionally including one of oxygen, sulfur or NR$_{12}$ wherein R$_{12}$ is as defined above.

In the description and claims hereinafter each of A, R', R, R$_1$, R$_2$, R$_3$, R$_4$, R$_5$, R$_6$, R$_7$, R$_8$, R$_9$, R$_{10}$, R$_{11}$, R$_{12}$, R$_{20}$, R$_{21}$, R$_{22}$, W, W$_1$, W$_2$, W$_3$, X, Y, Q and m is as defined above unless otherwise stated.

Where any of the substituents is or comprises halogen, such halogen is conveniently selected from fluoro, chloro, bromo, and iodo, especially fluoro, chloro or bromo.

Alkyl moieties are straight or branched chain and contain 1 to 8 preferably 1 to 4 carbon atoms.

Alkenyl and alkynyl moieties are straight or branched chain and contain 2 to 8 preferably 2 to 4 carbon atoms.

"Aryl" moieties are conveniently phenyl, naphthyl, pyridyl, quinolyl, pyridyl-N-oxide, pyrimidinyl, pyrazinyl, thienyl, furyl, pyrrolyl, oxazolyl, thiazolyl, isoxazolyl, isothiazolyl, imidazolyl, pyrazolyl, oxadiazolyl, or thiodiazolyl, especially phenyl, pyridyl, quinolyl, pyridyl-N-oxide, pyrimidinyl, pyrazinyl, thienyl, furyl or isothiazolyl. When these groups are substituted the substituents are preferably one to three in number and selected from the meanings given above for R$_{20}$ especially halogen, alkyl, haloalkyl, alkoxy, haloalkoxy, nitro, cyano, alkylthio, amino, alkylamino, dialkylamino or hydroxy. Specially preferred "Aryl" moieties are phenyl and pyridyl, especially phenyl.

Examples of rings formed by R$_3$ and R$_4$ or R$_7$ and R$_8$ together with the nitrogen atoms to which they are attached include pyrrolidine, imidazolidine, pyrazolidine, piperidine, piperazine, morpholine, thiomorpholine.

Ring A is preferably phenyl, 2-pyridyl or 3-isothiazolyl substituted as defined above.

The term "substituted ammonium cation" refers to an ammonium cation substituted by a C$_{1-20}$alkyl, di-C$_{1-20}$alkyl, tri-C$_{1-20}$alkyl, tetra-C$_{1-20}$alkyl, hydroxy-C$_{1-5}$alkyl, di(hydroxy-C$_{1-5}$alkyl), tri(hydroxy-C$_{1-5}$alkyl), C$_{1-5}$alkoxy-C$_{1-5}$alkyl, hydroxy-C$_{1-5}$alkoxy-C$_{1-5}$alkyl or C$_{1-5}$alkoxycarbonyl-C$_{1-5}$alkyl group.

A particular group of compounds is represented by formula Ia

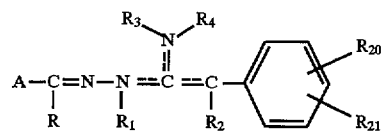

wherein A is defined for formula I

R' is the group

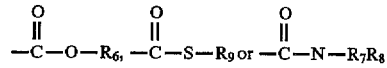

R is hydrogen or C$_{1-8}$alkyl

R$_1$ is hydrogen, C$_{1-8}$alkyl, C$_{1-4}$alkoxy-C$_{1-4}$alkyl, hydroxy-C$_{1-8}$alkyl, aryl or substituted aryl;

each of R$_2$, R$_3$ and R$_4$ is independently selected from the values of R$_1$ or C$_{1-8}$alkoxy or C$_{1-8}$alkylamino; R$_3$ and R$_4$ may be taken together to form a C$_{3-6}$alkylene bridge, optionally including one of oxygen, sulfur or N—R$_5$;

m is zero or one

Q is oxygen, sulfur or N—R$_5$

R$_5$ is hydrogen or C$_{1-8}$alkyl

R$_6$ is hydrogen, C$_{1-8}$alkyl optionally substituted with 1 to 6 halogen atoms, C$_{1-4}$alkoxy-C$_{1-4}$alkyl, unsubstituted or substituted phenyl, alkali or alkaline earth cation, ammonium cation, substituted ammonium cation, phosphonium cation, trialkylsulfonium cation, trialkylsulfoxonium cation or the group

W$_3$

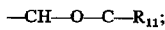

R$_{10}$

R$_9$ is C$_{1-8}$alkyl, C$_{2-8}$alkenyl, phenyl or benzyl;

each of R$_7$ and R$_8$ is independently hydrogen or C$_{1-8}$alkyl; or R$_7$ and R$_8$ are taken together to for a C$_{3-6}$alkylene bridge, optionally including one of O, S or NH;

each of R$_{10}$ and R$_{11}$ is independently hydrogen, C$_{1-8}$alkyl or C$_{1-4}$alkoxy-C$_{1-4}$alkyl;

each of W$_1$ and W$_2$ is independently nitrogen or CH

W$_3$ is oxygen or sulfur each of R$_{20}$, R$_{21}$ and R$_{22}$ is independently hydrogen, C$_{1-8}$alkyl optionally substituted by 1 to 6 halogen atoms, C$_{1-8}$alkoxy optionally substituted with 1 to 6 halogen atoms, C$_{1-8}$alkenyloxy optionally substituted with 1 to 6 halogen atoms, C$_{2-8}$alkynyloxy, C$_{1-8}$alkylthio, phenyl, phenoxy, hydroxy, halogen, nitro, cyano, amino, C$_{1-8}$alkylamino or di-C$_{1-8}$alkylamino; and the dotted lines indicate a double bond in one of the three positions.

Due to the requirement for the imino bond in one of the three indicated positions in formula Ia, which bond is not fixed to one position only because of tautomerism, only three of the four radicals R$_1$, R$_2$, R$_3$ and R$_4$ can be accommodated in any one structure.

Within the compounds of formula Ia those are preferred wherein A is the group

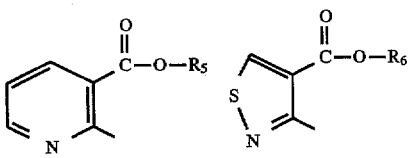

and particularly those of formula Ib or Ic

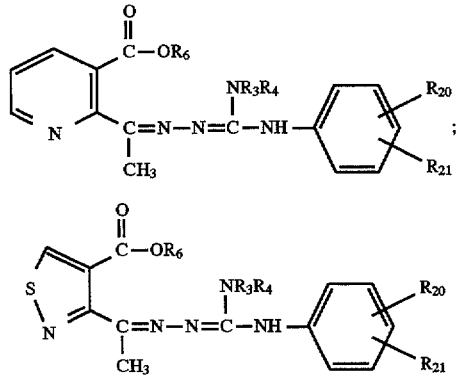

wherein the substituents are as defined for formula Ia.

Within formulae I, Ia, Ib and Ic those compounds are preferred wherein $R_{20}$ is hydrogen, methyl, methoxy, trifluoromethyl or halogen and $R_{21}$ is hydrogen or halogen are preferred.

Also preferred within formulae I, Ia, Ib and Ic are those compounds wherein each of $R_3$ and $R_4$ is independently hydrogen, $C_{1-4}$alkyl, $C_{1-4}$alkoxy, $C_{1-4}$hydroxyalkyl or phenyl; or $R_3$ and $R_4$ taken together are a $C_{3-5}$alkylene bridge optionally including one of oxygen, sulfur or NH in the ring.

Also preferred within formulae I, Ia, Ib and Ic are those compounds wherein $R_6$ is hydrogen, sodium cation, ammonium cation, $C_{1-20}$alkylammonium cation, di-$C_{1-5}$alkylammonium cation, hydroxy-$C_{1-5}$alkylammonium cation, di-(hydroxy-$C_{1-5}$alkyl)ammonium cation, hydroxy-$C_{1-5}$alkylammonium cation or the

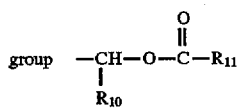

wherein $R_{10}$ and $R_{11}$ are as defined for formula Ia whereby preferably $R_{10}$ is hydrogen, methyl, ethyl or sec-butyl; and $R_{11}$ is hydrogen, methyl, ethyl, n-propyl, sec-butyl or tert-butyl.

Also preferred within formulae I, Ia, Ib and Ic are those compounds wherein $R_6$ is hydrogen, sodium cation, isopropylammonium cation, tetra-decylammonium cation, 2-hydroxyethylammonium cation, di-2-hydroxyethylammonium cation, 2-(2-hydroxyethoxy) ethylammonium action, butyryloxymethyl, 1-(2-methylbutyryloxy)ethyl, pivaloyloxymethyl, 1-(pivaloyloxy)ethyl or 1-(propionyloxy)ethyl Also preferred within formulae I, Ia, Ib and Ic are those compounds wherein $R_3$ is hydrogen, ethyl, propyl or butyl, and $R_4$ is hydrogen, ethyl or propyl; or $R_3$ and $R_4$ taken together form a diethylthio bridging group Also preferred within formulae I, Ia, Ib and Ic are those compounds wherein each of $R_{20}$ and $R_{21}$ is independently hydrogen, chloro or fluoro Also preferred within formulae I, Ia, Ib and Ic are chose compounds wherein $R_6$ is hydrogen, sodium cation, isopropylammonium cation, tetra-decylammonium cation, 2-hydroxyethylammonium cation or di-2-hydroxyethylammonium cation.

Another group of preferred compounds comprises those of formula Id

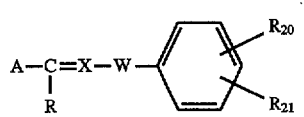

wherein W is

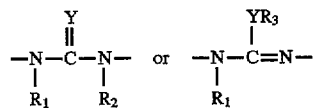

R and $R_1$ taken together form 2 to 4 membered alkylene, alkenylene or mixed alkylenealkenylene bridge which may bear one or more substituents selected from halogen, alkyl, alkoxy, phenyl or substituted phenyl and in which any methylene may be replaced by a group selected from oxygen, sulfur, $NR_{12}$, carbonyl or thiocarbonyl; wherein $R_{12}$ is hydrogen, alkyl, alkoxy, phenyl or substituted phenyl and all remaining substituents are as defined above for formula I.

Within compounds I and Id A is preferably phenyl, 2-pyridyl or 3-iso-thiazolyl substituted as defined.

Also preferred are compounds of formula I and Id wherein $R_{20}$ is hydrogen, halogen (especially fluoro, chloro or bromo), $C_{1-4}$alkyl (especially methyl or ethyl), $C_{1-4}$haloalkyl (especially trifluoromethyl) or $C_{1-4}$alkoxy (especially methoxy).

Also preferred are compounds of formula I and Id wherein $R_{21}$ is hydrogen, $C_{1-4}$alkyl (especially methyl), $C_{1-4}$alkoxy (especially methoxy) and halogen (especially fluoro or chloro).

Also preferred are compounds of formula I and Id wherein X is N.

Also preferred are compounds of formula I and Id wherein W is

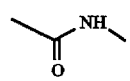

Also preferred are compounds of formula I and Id wherein R and $R_1$ taken together represent —$(CH_2)_2$— or —$(CH_2)_3$—.

Also preferred are compounds of formula I and Id wherein A represents phenyl or 2-pyridyl each substituted ortho to the position of attachment by a carboxyl group in free acid or salt form.

When in salt form the carboxyl group in formula I is preferably in alkali metal or substituted ammonium salt form.

Also preferred are compounds of formula I and Id wherein $R_{20}$ represents hydrogen, halogen, $C_{1-4}$alkyl, $C_{1-4}$haloalkyl or $C_{1-4}$alkoxy; $R_{21}$ represents hydrogen, $C_{1-4}$alkyl $C_{1-4}$alkoxy or halogen; X is N; W is

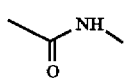

R and $R_1$ taken together are —$(CH_2)_2$—, —$(CH_2)_3$— or —CH=CH—; A is phenyl or 2-pyridyl each substituted ortho to the position of attachment by a carboxy group in free acid or salt form.

Also preferred are compounds of formula I and Id wherein A is pyridyl substituted in ortho position by a carboxy group, in free acid or salt form, X=N, Y=O, $R_{20}$=H, F, Cl, $R_{21}$=H, F, R and $R_1$ taken together are —$(CH_2)_2$— or —$(CH_2)_3$—.

Also preferred are compounds of formula I and Id wherein $R_{20}$ represents hydrogen, $C_{1-4}$alkyl, $C_{1-4}$alkoxy or halogen;

$R_{21}$ represents hydrogen or halogen

W is

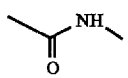

X is N;

R and $R_1$ taken together are —$(CH_2)_2$— or —$(CH_2)_3$— or CH=CH—.

Combinations of preferred meanings given above for formulae I, Ia, Ib, Ic and Id are especially preferred.

The compounds of formula I may be prepared analogously to known methods, they can thus be prepared according to the invention as follows.

A) when R and $R_1$ are independently a) reacting a compound of formula II

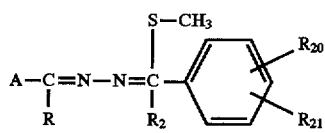

with a compound of formula III

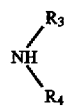

b) reacting a compound of formula IV

with a compound of formula V

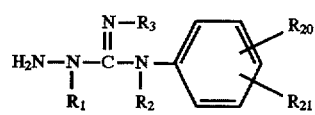

wherein A, R, $R_1$, $R_2$, $R_3$, $R_4$, $R_{20}$ and $R_{21}$ are as defined above; or B) when R and $R_1$ are taken together as defined a) reacting a compound of formula X

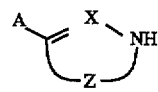

with a compound of formula XI, XII, or XIII

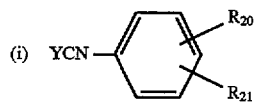

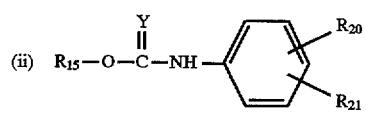

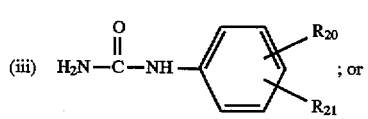

wherein Z is as defined above for R and $R_1$ taken together $R_{15}$ is a protecting group and the remaining substituents are as defined above.

b) when A bears a carboxy group and X is N, ring-opening a compound of formula Ip

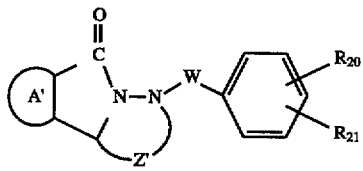

wherein A' is a ring which upon ring-opening of Ip forms a group A which is ortho substituted by a carboxy group in free acid, salt or ester form;

Z' is a 1 to 3 membered alkylene, alkenylene or mixed alkylene-alkenylene bridge which may bear one or more substituents selected from halogen, $C_{1-4}$alkyl, $C_{1-4}$alkoxy, phenyl or substituted phenyl and in which any methylene may be replaced by a group selected from oxygen, sulfur, $NR_{12}$, carbonyl or thiocarbonyl whereby the attachment of Z' to the lactam is via a double bond, and the remaining substituents are as defined above.

Compounds thus obtained bearing a carboxyl group may be recovered in free acid, salt or ester form and those bearing a thiocarboxyl group in free acid or ester form and may be recovered from the reaction mixture in which they are formed and purified in conventional manner.

Process Aa) is conveniently carried out in a solvent which is inert under the reaction conditions, e.g. methanol, ethanol, methylene chloride, toluene or dimethylformamide. A suitable reaction temperature may vary from –10° C. to the boiling point of the solvent used, and preferably is about reflux temperature or moderately below reflux temperature.

Process Ab) is conveniently carried out in a solvent which is inert under the reaction conditions, e.g. methanol, ethanol, methylene chloride, toluene or dimethylformamide. A suitable reaction temperature may vary from –10° C. to the boiling point of the solvent used, and preferably is about room temperature or moderately above or below room temperature, e.g. between 15° and 25° C.

Process Ba)(i) may conveniently be carried out in the presence of an inert preferably organic solvent such as an ether e.g. diethylether, an amide e.g. dimethylformamide, a halogenated hydrocarbon e.g. methylene dichloride, an ester such as ethyl acetate, a nitrile such as acetonitrile or a hydrocarbon such as toluene and at room temperature or below e.g. at 0° to 25° C.

Process Ba)(ii) may be conveniently be carried out in the presence of an inert preferably organic solvent e.g. an alcohol such as ethanol, a nitrile such as acetonitrile, a hydrocarbon such as toluene or an ether such as diethylether or tetrahydrofuran and at reflux temperature of the reaction mixture.

Process Ba)(iii) may be conveniently be carried out in the presence of an inert preferably organic solvent such as those suited for process a)ii) and at reflux temperature of the reaction mixture.

Process B)b) may be carried out for example by addition of a base at elevated temperature. Suitable bases are alkali or alkaline earth metal hydroxides such as NaOH. Suitable solvents include water, alcohols, e.g. methanol. Suitable temperatures are e.g. from 30° to 80° C.

Depending on reaction conditions and work-up procedures the compounds of formula I wherein A is carboxyl or thiocarboxyl substituted may be recovered in free acid, ester or, for carboxyl, salt form. Such forms may be interconverted in conventional manner. Acid addition salts may also be prepared in conventional manner.

The starting materials and reagents employed in the process described herein are either known or, insofar as they are not known, may be produced in a manner analogous to the processes described herein or to known processes.

The reaction schemes A and B illustrate methods by which the compounds of formulae X and Ip may be prepared. Other intermediates of the formulae X and Ip may be prepared analogously.

Reaction Scheme A

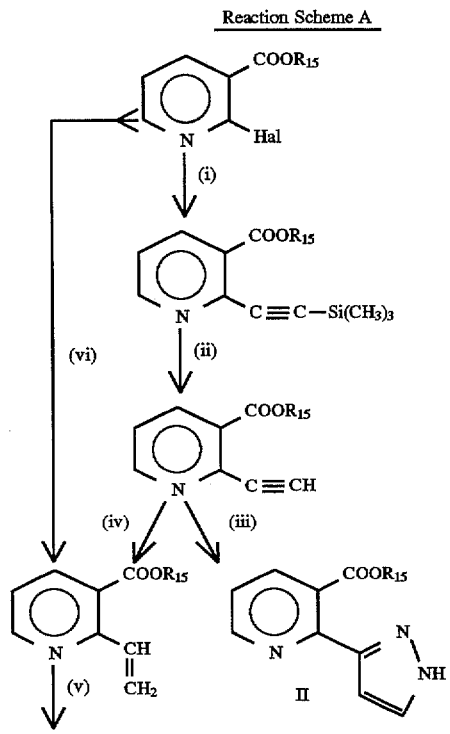

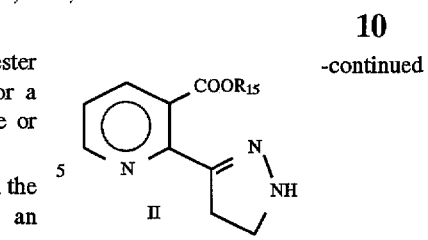

Reaction Scheme B

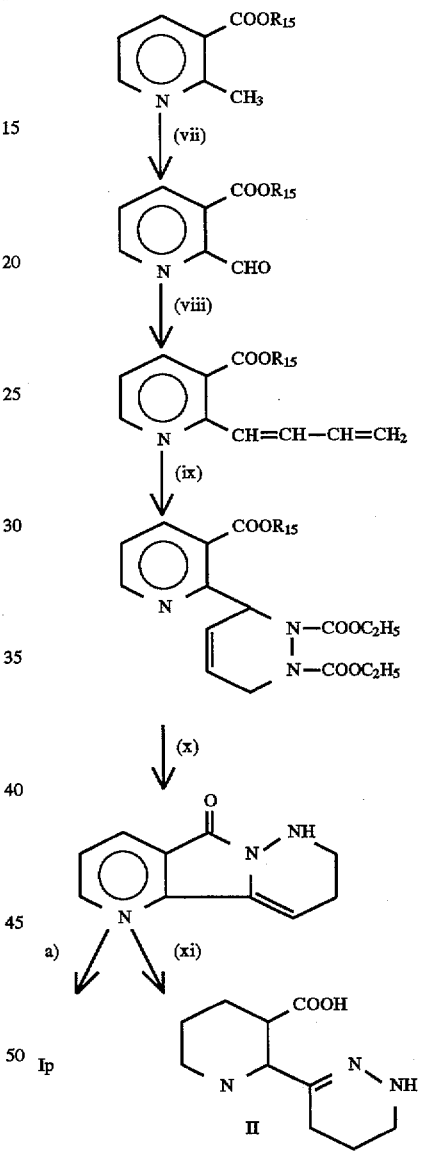

$R_{15}$ = protecting group
Hal = halogen

Process Conditions (i) react with ethynyltrimethylsilane, palladium catalyst, triethylamine as solvent, room to elevated temperatures under $N_2$ atmosphere. When $R_3$ is 2-pyridyl (as shown) Hal is preferably I, when $R_3$ is phenyl Hal is preferably Br.

(ii) React with $KF.2H_2O$, solvent DMF, room temperature.

(iii) and (v) cycloaddition with a diazo compound, e.g. diazomethane in diethylether, dichloromethane or diethylether as solvent for starting material, temperatures cool (ice-bath)

(iv) hydrogenation (H$_2$) with e.g. Lindlar catalyst, solvent ethylacetate, room temperature.

(vi) (C$_4$H$_9$)$_3$SnCH=CH$_2$ with palladium catalyst, solvent THF; reflux.

(vii) Oxidation e.g. with SeO$_2$, solvent dioxane, reflux under nitrogen atmosphere.

(viii) React with ($\phi$)$_3$P=CH—CH=CH$_2$ (prepared from ($\phi$)$_3$P$^+$—CH$_2$—CH=CH$_2$.Br$^-$ and BuLi under N$_2$), reflux; diethylether as solvent.

(ix) React with C$_2$H$_5$OOOC—N=N—COOC$_2$H$_5$, solvent toluene, reflux under N$_2$.

(x) cyclization using strong acid e.g. H$_2$SO$_4$, solvent water/acetone.

(xi) hydrolyze with base followed by acidification; methanol/water as solvent.

The compounds of this invention wherein R and R$_1$ are independent can exist in one of several tautomeric forms. For example, when R$_1$, R$_2$, R$_3$ and R$_4$ are hydrogen, the compounds are represented by the following:

cocklebur, sicklepod, annual morning glory, lambsquarter, teaweed and smartweed.

The compounds of the present invention, when applied pre-emergence, demonstrate high levels of herbicidal activity on both broadleaf and grass weeds.

In the use of the compounds of formula I for combatting weeds, a compound of formula I, or mixtures thereof, can conveniently be employed as herbicidal compositions in association with acceptable diluent(s) for application to the weed or its locus. Such compositions also form part of the present invention.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of

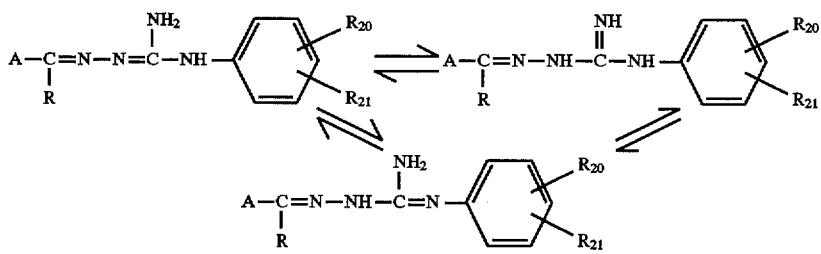

All tautomeric forms are encompassed by the present invention.

The novel compounds of formula (I) are useful for the control of weeds, using pre- and/or post-emergent treatments. They are also useful as plant growth regulators. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one hundredth to 10 pounds per acre especially one-tenth or less to ten pounds per acre. The application of a compound of the present invention to the "locus" of the weed includes application to the seeds, the plant (weed) or parts of the plant, or the soil.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The term "herbicide" as used herein, refers to an active ingredient which modifies the growth of plants because of its phytotoxic or plant growth regulating properties so as to retard the growth of the plant or damage the plant sufficiently to kill it.

While some of the compounds of the present invention have activity on grass weeds, the compounds, in general, demonstrate a higher level of herbicidal activity on broadleaf plants when applied postemergence. Broadleaf plant (weed) species on which the compounds of the present invention show effective herbicidal activity include, but are not limited to, mustard, pigweed, velvetleaf, jimsonweed, course, be present depending on the intended use, the physical properties of the compound and the mode of application. Concentrate forms of a composition intended to be diluted before use generally contain between 2 and 90%, preferably between 5 and 81% by weight of active ingredient.

Useful formulations of the compounds of formula I include dusts, granules, suspension concentrates, wettable powders, flowables and the like. They are obtained by conventional manner, e.g. by mixing a compound of formula I with the diluent(s) and optionally with other ingredients.

Alternatively, the compounds of formula I may be used in micro-encapsulated form.

The compounds of formula I can be combined with a cyclodextrin to make a cyclodextrin inclusion complex for application to the weed, acari or their loci.

Agriculturally acceptable additives may be employed in the herbicidal compositions to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomacous earth, for liquid concentrate forms for example a hydrocarbon such as xylene or an alcohol such as isopropanol, and for liquid application forms e.g. water or diesel oil.

Compounds of c his invention may be advantageously combined with other herbicides for broadspectrum weed control. Examples of herbicides which can be combined with a compound of the present invention include those selected from the carbamates, thiocarbamates, chloroacetamides, triazines, dinitroanilines, benzoic acids, glycerol ethers, pyridazinones, uracils and ureas for controlling a broad spectrum of weeds. The compounds of this invention may also have a potentiating effect on such herbicides.

The compositions of this invention can also comprise other compounds having biological activity, e.g. compounds having antidotal, fungicidal, insecticidal, acaricidal or insect attractant activity.

The compounds of formula Ip also exhibit herbicidal activity as described above.

The following examples are provided to illustrate the practice of the present invention. Temperature is given in degrees Centigrade. "RT" means room temperature. Parts and percentages are by weight. The symbols *, # and + when used in connection with melting points mean "gas", "softens" and "decomposes", respectively.

EXAMPLE 1

A solution of 2-acetylnicotinic acid 4-(3-fluorophenyl) thiosemicarbazone (8.0 g, 24.1 mmol) in 50 ml of methanol is treated with sodium methoxide (2.8 g, 48.2 mmol) in methanol, after which methyl iodide (3.4 g, 24.1 mmol) is added. After 1 hr. the solvent is removed, and the residue is taken up in water and washed with chloroform. The chloroform layer is discarded, and the aqueous layer is made acidic with conc. HCl and extracted with chloroform. The organic layer is washed with water, dried and stripped of solvent to give 2-acetylnicotinic acid S-methyl-4-(3-fluorophenyl)isothiosemicarbazone, a yellow solid.

EXAMPLE 2

A mixture of the product of Example 1 (2.0 g, 5.8 mmol) and sodium methoxide (0.3 g, 5.8 mmol) in 25 ml of methanol is treated with diethylamine (0.44 g, 6.0 mmol), and the mixture is heated to reflux for 4 hours. The reaction mixture is cooled and the solvent is removed. The residue is taken up in water, and the aqueous phase is washed with chloroform, and filtered. The filtrate is adjusted to pH6 with 2NHCl and extracted with chloroform. The organic layer is washed with sat. NaCl, dried and stripped of solvent to give 2-[methyl(3-carboxy-2-pyridyl)methylene]-N,N-diethyl-N'-(3-fluorophenyl)hydrazinecarboximidamide, a yellow solid (compound 1 under Table A).

EXAMPLE 3

A mixture of the product of Example 1 (2.0 g, 5.8 mmol), sodium methoxide (0.33 g, 5.8 mmol) and thiomorpholine (0.6 g, 5.8 mmol) in 25 ml of ethanol is heated to 55° for 3 hr. An additional 0.3 g of thiomorpholine is added and heating at 55° is continued overnight. The reaction mixture is cooled and is then worked up following the procedures in Example 2 to give 2-[methyl(3-carboxy-2-pyridyl) methylene]-N,N-ethylenethioethylene-N'-(3-fluorophenyl) hydrazinecarboximidamide, a bright yellow solid (compound 2 under Table A).

EXAMPLE 4

A mixture of the product of Example 1 (1.9 g, 5.5 mmol), n-butylamine (0.45 g, 6.2 mmol) and sodium methoxide (0.3 g, 5.5 mmol) in 25 ml of ethanol is heated to reflux, under $N_2$, for 18 hr. The reaction mixture is cooled and worked up as above to give an off-white solid, which is then treated with hot benzene. The benzene-insoluble material is filtered off and the filtrate is evaporated to give 2-[methyl(3-carboxy-2-pyridyl)methylene]-N-butyl-N'-(3-fluorophenyl) hydrazinecarboximidamide, a white solid (compound 3 under Table A).

EXAMPLE 5

Following the procedures of Example 2, 3 or 4, the final hydrazone compounds 4–15 under Table A are prepared from the corresponding amine and 2-acetylnicotinic acid S-methyl-4-(substitutedphenyl)isothiosemicarbazone.

EXAMPLE 6

Following the procedure of Example 1 and 2, 3 or 4, 3-acetyl-4-isothiazolecarboxylic acid is reacted with each of S-methyl-4-(3-chlorophenyl)isothiosemicarbazone, S-methyl-4-(3-fluorophenyl)isothiosemicarbazone and S-methyl-4-(3,5-difluorophenyl)isothiosemicarbazone and the product treated with an amine to give the corresponding hydrazones.

EXAMPLE 7

A mixture of 3-fluorophenylthiourea (20.0 g, 166.7 mmol) and methyl iodide (24.8 g, 175.0 mmol) in 300 ml of ethanol is stirred at RT for 2 days. It is then heated to reflux for 30 min., cooled and stripped of solvent to give S-methyl-3-fluorophenylisothiourea hydroiodide, an orange solid.

A mixture of the above isothiourea salt (8.5 g, 27.0 mmol) and hydrazine (1.4 g, 27.0 mmol) in 80 ml of ethanol is heated to reflux for 4 hr. The mixture is cooled and the solvent removed. The residue is diluted with 80 ml of water and filtered. A 20 ml aliquot of the resulting aqueous filtrate (2.0 g, 11.9 mmol) is mixed with 2-acetylnicotinic acid (2.0 g, 11.9 mmol) in 6 ml of methanol and stirred at RT overnight. A bright yellow solid is collected by filtration and dried to give 2-[methyl(3-carboxy-2-pyridyl)methylene]-N-(3-fluorophenyl)hydrazinecarboximidamide, (compound 16).

EXAMPLE 8

Following the procedure of Example 7, 3-acetyl-4-isothiazole carboxylic acid (2.05 g, 12.0 mmol) and N-(3-fluorophenyl)hydrazinecarboximidamide (3.55 g, 12.0 mmol) are reacted together to give 2-[methyl(4-carboxy-3-isothiazolyl)methylene]-N-(3-fluorophenyl) hydrazinecarboximidamide, (compound 17).

EXAMPLE 9

To a solution of compound 2 (from Example 3) (1.0 g) in 10 ml of methanol is added 1 equivalent of sodium methoxide. The mixture is stirred at RT for 5–10 min., after which the solvent is removed and the residue is dried to give the sodium salt of compounds 2.

Following the above procedures, each of the acids prepared in Examples 2 and 4 through 8 above is treated with 1 equivalent of sodium methoxide to give the corresponding sodium salt.

EXAMPLE 10

Following the procedures of Example 9, compound 1 (from Example 2) is treated with 1 equivalent of each of the compounds under column I to give the corresponding acid salt.

I aqueous ammonium hydroxide
isopropylamine diisopropylamine
2-hydroxyethylamine
di-2-hydroxyethylamine
2-(2-hydroxyethoxy)ethylamine
dimethylamine
octylamine
tetradecylamine

EXAMPLE 11

A suspension of compound 3 in 20 ml of methanol is created with diazomethane until the yellow color of the solution persists. The solvent removed in vacuo to give 2-[methyl(3-methoxycarbonyl-2-pyridyl)methylene]-N-butyl-N'-(3-fluorophenyl)hydrazinecarboximidamide.

EXAMPLE 12

A mixture of the sodium salt of compound 1 (3.0 mmol) and chloromethyl acetate (0.4 g, 3.5 mmol) in 18 ml of DMF is stirred at RT for 3 days. The reaction mixture is poured onto ice. The solid which precipitates is collected by filtration, is washed with water and is air-dried. It is stirred in 50 ml of chloroform for 2 hours and is filtered. The filtrate is evaporated and triturated with ether to give the crude product. Purification by prep. TLC gives 2-[methyl(3-acetyloxy-methoxycarbonyl-2-pyridyl)-methylene]-N,N-diethyl-N'-(3-fluorophenyl)hydrarazinecarboximidamide.

TABLE A

| Cpd | $R_6$ | R | $R_2$ | $R_3$ | $R_4$ | $R_{20}$ | $R_{21}$ |
|---|---|---|---|---|---|---|---|
| 1 | H | $CH_3$ | H | $CH_2CH_3$ | $CH_2CH_3$ | 3-F | H |
| 2 | H | $CH_3$ | H | $CH_2CH_2-S-CH_2CH_2$ | | 3-F | H |
| 3 | H | $CH_3$ | H | $CH_2CH_2CH_2CH_3$ | H | 3-F | H |
| 4 | H | $CH_3$ | H | $CH_2CH_3$ | $CH_2CH_3$ | H | H |
| 5 | H | $CH_3$ | H | $CH_2CH_3$ | $CH_2CH_3$ | 3-Cl | H |
| 6 | H | $CH_3$ | H | $CH_2CH_3$ | $CH_2CH_3$ | 3-$CF_3$ | H |
| 7 | H | $CH_3$ | H | $CH_2CH_3$ | $CH_2CH_3$ | 3-$CH_3$ | H |
| 8 | H | $CH_3$ | H | $CH_2CH_3$ | $CH_2CH_3$ | 3-$OCH_3$ | H |
| 9 | H | $CH_3$ | H | $CH_2CH_3$ | $CH_2CH_3$ | 4-Cl | H |
| 10 | H | $CH_3$ | H | $CH_2CH_3$ | $CH_2CH_3$ | 4-F | H |
| 11 | H | $CH_3$ | H | $CH_2CH_3$ | $CH_2CH_3$ | 3-Cl | 5-F |
| 12 | H | $CH_3$ | H | $CH_2CH_3$ | $CH_2CH_3$ | 3-F | 5-F |
| 13 | H | $CH_3$ | H | $OCH_3$ | H | 3-F | H |
| 14 | H | $CH_3$ | H | $CH_2CH_2OH$ | H | 3-F | H |
| 15 | H | $CH_3$ | H | $C_6H_5$ | H | 3-F | H |

EXAMPLE 13

Preparation of 2-[1-(3-fluorophenylaminocarbonyl)-2-pyrazolin-3-yl]nicotinic acid, ethylester and sodium salt (Table B cmpd. no. 19)

a) Ethyl ester 3.85 g (17.6 m.M) of 2-(1-pyrazolin-3-yl)-nicotinic acid ethyl ester are dissolved in 30 ml of ether. 2.6 g (19 m.M) of 3-fluorophenylisocyanate and a few drops of triethylamine are added and the mixture stirred at RT for 3 hrs. The precipitated yellow solid is filtered, washed with ether and dried under vacuum to yield the ethyl ester of the title compound, m.p. 117°–119.5°.

b) Free acid 1.70 g (4.8 mM) of the title compound as ester are dissolved in 10 ml of methanol and 0.15 g of LiOH.H$_2$O in 10 ml of water added. The resulting slurry is warmed to 50° with stirring until all solid has dissolved. The methanol is removed on a rotovapor, water added, the solution extracted twice with ethylacetate and then acidified with 1M H$_2$SO$_4$. The resulting yellow precipitate is filtered rinsed with water and dried to yield the corresponding free acid. Recrystallized from Et$_2$O/THF to give m.p. 217°–219°.

c) Sodium salt 1.2 g of the free acid of the title compound are slurried in 20 ml of methanol and 0.8 g of 25% sodium methoxide added to give a clear solution. This is evaporated to dryness and dried under vacuum at 60°. The sodium salt of the free acid of the title compound is obtained m.p. 281°–283°.

EXAMPLE 14

Preparation of 2-[1-(3,5-difluorophenylaminocarbonyl)-pyrazol-3-yl]-nicotinic acid sodium salt (Table B cmpd. no. 23)

0.95 g (4.5 mM) of 2-(pyrazol-3-yl)-nicotinic acid sodium salt are stirred in 20 ml of DMF and 0.7 g (4.5 mM) of 3,5-difluorophenyl isocyanate added. After stirring for 1 hr at RT, a further 0.21 g of isocyanate in DMF are added. The DMF is stripped-off on a Kugelrohr and the resulting solid stirred with 4 ml water and filtered. The filtrate is chromatographed on a reverse phase column with 100 ml of water followed by 100 ml water-methanol. The product containing fraction was lypholized yield the title product m.p. 165°–170° C.

EXAMPLE 15

Preparation of 2-[1-(3,5-difluorophenylaminocarbonyl)-1,4,5,6-tetrahydropyrazine-3-yl]-nicotinic acid and sodium salt (Table B cmpd. no. 24)

a) Free acid 0.27 g of 1-(3,5-difluorophenylaminocarbonyl)-1,2,3,9-tetrahydropyridino[2',3',3,4]pyrrolo[1,2-b]pyridazin-9-one (cmpd Ip R$_3$=pyridinyl, Z' is =C—CH$_2$—CH$_2$—, W=—C—NH.

O

R$_1$=3-F, R$_2$=5-F) are dissolved in 20 ml of methanol and 0.15 g of NaOH dissolved in 20 ml of hot water added. The reaction mixture is placed in a hot water bath and stirred at 60° with the addition of a further 0.35 g of NaOH. Stirring is continued until reaction complete (TLC with ethylacetate as eluant) and the reaction mixture is cooled and concentrated to remove methanol. The resulting mixture is rinsed three times with ethylacetate, acidified with 1M H$_2$SO$_4$ and extracted three times with ethylacetate.

The extract is dried over MgSO$_4$, filtered and dried in vacuum to yield the free acid of the title compound.

b) The sodium salt is prepared analogously to example 13c).

The compounds shown in Table B below may be prepared analogously to examples 13, 14 and 15 above.

Cmpd No. 24 NMR $^1$H-NMR (DMSOd$_6$) δ 1.93 (2H, m); 2.81 (2H, broad t), 3.77 (2H, broad t), 6.82 (1H, t of t); 7.3–7.7 (3H, m); 7.92 (1H, d of d); 8.68 (1H, d of d); 8.88 (1H broad s).

TABLE B

| Cpd | W₁ | Z | R₆ | X | R₂₀ | R₂₈ | acid | Na salt |
|---|---|---|---|---|---|---|---|---|
| 18 | N | $-(CH_2)_2-$ | H | O | 3-F | 5-F | | 284-5* |
| 19 | N | $-(CH_2)_2-$ | H | O | 3-F | H | 217-9 | 281-3+ |
| 20 | N | $-(CH_2)_2-$ | H | O | 3-Cl | 5-Cl | | 295-8 |
| 21 | N | $-(CH_2)_2-$ | H | O | 3-CH₃ | H | | 265-74* |
| 22 | N | $-(CH_2)_2-$ | H | O | 3-OCH₃ | H | H | 270-4*+ |
| 23 | N | $-CH=CH-$ | H | O | 3-F | 5-F | | 165-70* |
| 24 | N | $-(CH_2)_3-$ | H | O | 3-F | 5-F | | 160-200* 295 (blackened) |
| 25 | N | $-(CH_2)_3-$ | H | O | 3-F | H | | 215 |
| 26 | N | $-(CH_2)_3-$ | H | O | 3-Cl | H | | 210 |
| 27 | N | $-CH=CH-$ | H | O | 3-F | H | 147-154* | |
| 28 | N | $-(CH_2)_2-$ | H | O | 3-Cl | H | 174-184 | 282-288 |
| 29 | N | $-(CH_2)_2-$ | H | O | H | H | | 276-277 |
| 30 | CH | $-(CH_2)_2-$ | H | O | F | F | | |
| 31 | CH | $-(CH_2)_2-$ | H | O | F | H | | |
| 32 | CH | $-(CH_2)_2-$ | H | O | Cl | H | | |

EXAMPLE 16

Preparation of:

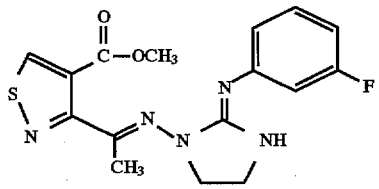

(Cmpd. #33 A=thiazol-3-yl; R'=4-methoxycarbonyl, R=CH₃; X=N,

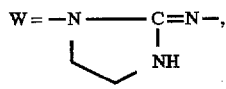

R₂₀=3-F, R₂₁=H)

a) 1.4 g of methyl iodide is added to a solution of 1-(3-fluorophenyl)-2-thiourea in 60 ml of methanol. The solution is refluxed for 2 hrs, cooled and evaporated to dryness under reduced pressure to give a crystalline material which is filtered and washed several times with ether to yield N-(3-fluorophenyl)-S-methyl-isothiuromium iodide.

b) A mixture of 3.4 g of 2-aminoethylhydrazine, 5.7 g of N-(3-fluorophenyl)-S-methyl-isothiuromium iodide and ethanol is refluxed for 1½ hrs. The mixture is cooled and evaporated to dryness. The residue is dissolved in dilute HCl, acidified to pH3 and washed with ether. The resulting aqueous solution is made alkaline with conc. aqueous ammonia extracted with ethylacetate, dried over MgSO₄ and evaporated to dryness. 3.0 g of this residue and 4.0 g of carboxy (3-acetyl-isothiazol-4-yl), methylate are dissolved in 30 ml of methanol and stirred overnight to 40°–45°. The solvent is evaporated and the mixture separated by flash chromatography (ethylacetate:hexane=1:1→6:4) to give the title compound. (Cmpd. #33)

The corresponding lithium salt may be prepared by reacting 3.05 g of ester dissolved in ethanol and water at 40° for 3 hrs. Drying and concentration of the solution yields the desired lithium salt m.p. 228°–32° (Cmpd. #34)

INTERMEDIATE COMPOUNDS

EXAMPLE A a) Preparation of 2-(2'-Trimethylsilylethylt)nicotinic acid ethyl ester 6.65 g (24 mM) of 2-iodonicotinic acid ethyl ester 3.0 g (30.6 mM) of (trimethylsilyl)acetylene, 0.19 g of CuI are mixed with stirring and under nitrogen with 40 ml of triethylamine. 0.38 g of palladium catalyst (($\phi_3$P)₂PdCl₂) are added resulting in a strongly exothermic reaction. On completion the reaction mixture is cooled to RT, diluted with 70 ml of ether and 50 ml of water added. After shaking the aqueous phase is separated and extracted three times with 30 ml ether. The ether phases are combined, washed with brine, separated, dried over MgSO, and after filtering the solvent evaporated under vacuum.

b) Preparation of 2-ethynylnicotinic acid ethyl ester 6.2 g of 2-(2'-trimethylsilylethynyl)-nicotinic acid ethyl ester are dissolved in 50 ml of DMF and 3 g of KF.2H₂O are added. After stirring at RT, the reaction mixture is diluted with 300 ml of ether filtered through celite, shaken with 150 ml of water and refiltered. The aqueous phase is extracted four times with 100 ml ether and the combined ether extracts dried over MgSO₄, filtered and dried under vacuum. The intermediate can be further purified by chromatography over silica with ethylacetate/hexane.

c) Preparation of 2-vinylnicotinic acid ethyl ester 3.45 g of 2-ethynylnicotinic acid ethyl ester are dissolved in 100 ml of ethyl acetate, 1 g of Lindler catalyst (5% Pd/CaCO₃ lead poisoned) added and stirred under H₂ (1 atm) until H₂ absorption ceases. The reaction mixture is filtered through celite and the solvent removed by evaporation to yield the title compound as an oil.

d) Preparation of 2-(1-pyrazolin-3-yl)-nicotinic acid ethyl ester

An excess of diazomethane in diethylether is added to 3.35 g of 2-vinylnicotinic acid ethyl ester and stirred at −10° overnight. Acetic acid is added until gas evolution ceases and the solvent is removed by evaporation under vacuum.

19 e) Preparation of 2-(pyrazol-3-yl)-nicotinic acid ethyl ester

An excess of diazomethane in diethylether at 0° is added to 3.91 g of 2-ethynylnicotinic acid ethyl ester and the solution allowed to warm to RT and let stand overnight. Acetic acid is added until no further gas evolves and the mixture is extracted with brine, dried over MgSO$_4$, filtered and the solvent removed by evaporation under vacuum to yield the title compound as an oil.

f) Preparation of 2-(pyrazol-3-yl)-nicotinic acid sodium salt 2.61 g of 2-(pyrazol-3-yl)-nicotinic acid ethyl ester are dissolved in 20 ml of methanol and 0.5 g of NaOH in 5 ml of water added. After standing for 1 hr the methanol is removed under vacuum and an additional 0.07 g of NaOH added and dissolved by warming. After standing for 1 hr the mixture is diluted with H$_2$O to 20 ml and divided into 4 aliquots of 5 ml. Each aliquot is chromatographed on Waters C18 sep. pak cartridge with 5 ml MeOH and 5 ml H$_2$O each. The aqueous phases are combined, adjusted to pH 7.7 with HCl and freeze dried to give the title compound, m.p. 260°.

EXAMPLE B a) Preparation of 2-formylnicotinic acid ethyl ester 16.9 g of 2-methylnicotinic acid ethyl ester, 22.9 g of selenium (IV) oxide and 240 ml dioxane are combined and refluxed overnight under nitrogen. The mixture is cooled to RT, filtered Through celite, and evaporated. The resulting red sludge is diluted with ethylacetate, filtered twice through celite and the solvent removed by evaporation under vacuum.

b) Preparation of 2-(1,3-butadienyl)-nicotinic acid ester

To an RT solution of propenylidinetriphenylphosphorane (prepared from 60.5 g of allyltriphenylphosphonium bromide in diethylether and 100 ml of 1.6 BuLi in hexane at −30°) is added 29.7 g of 2-formylnicotinic acid ethyl ester in portions over 40 minutes and the mixture refluxed with stirring for 30 mins. After cooling to RT 250 ml of water and 20 ml of 1M H$_2$SO$_4$ are added. The organic phase is separated and the remaining mixture extracted 3× with 250 ml ether and twice with methylene dichloride. The methylene dichloride extracts are added to 500 ml of hexane and filtered. The ether and methylene dichloride/hexane extracts are combined, concentrated, filtered to remove solids and the solvent removed by evaporation under vacuum to yield The title product as an oil. The product may be further purified by chromatography on silica with ethyl acetate/hexane.

c) Preparation of 2-(1,2-diethoxycarbonyl-1,2,3,6-terahydropyridazin-3-yl)-nicotinic acid ethyl ester 9.8 g of 2-(1,3-butadienyl)nicotinic acid ethyl ester and 9.2 g of diethyl-azodicarboxylate are mixed with 30 ml of toluene and heated to 80° under nitrogen. After 1 hr a further 3 g of diethyl-azodicarboxlate are added and after 3 hrs a further 5 g. After a further 4 hrs the reaction mixture is allowed to cool to RT and stirred overnight. The solvent is removed by evaporation under vacuum and the resulting oil chromatographed on silica gel and eluted with ethylacetate/hexane to give the title compound as black oil.

d) Preparation of 1,2,3,9-tetrahydropyridino[2'3':3,4]pyrrolo[1,2-b]pyridazin-9-one 6.6 g of 2-(1,2-diethoxycarbonyl-1,2,3,6-tetrahydropyridazin-3-yl)nicotinic acid ethyl ester are mixed with 15 ml water and 60 ml of H$_2$SO$_4$ added with cooling. The reaction mixture is heated under nitrogen to 120° over 1 hr in a hot oil bath. The mixture is slowly poured into 125 g Na$_2$CO$_3$ and 250 g of ice and 125 ml of water. The alkaline mixture is filtered through celite and repeatedly extracted with ethylacetate (8×100 ml) and the extracts dried over MgSO$_4$. After filtration the solvent is removed by evaporation under vacuum to yield the title compound which is recrystalized from CH$_3$CN.

e) Preparation of 1-(3,5-difluorphenylaminocarbonyl)-1,2,3,9-tetrahydropyridine[2'3':3,4]pyrrolo[1,2-b]pyridazin-9-one 0.48 g of 1,2,3,9-tetrahydropyridino[2'3':3,4]pyrrolo[1,2-b]pyridazin-9-one and 0.4 g of 3,5-difluorophenylisocyanate are mixed in methylene dichloride and a few drops of triethylamine added. After several hours of stirring at RT the mixture is rinsed twice with 1M H$_2$SO$_4$ and the aqueous phase backwashed with methylene chloride. After treating the methylene chloride solution with activated charcoal it is dried over MgSO$_4$ and after filtering the solvent removed by evaporation under vacuum. Recrystallization from CH$_3$CN yields the title compound m.p. 198°–208° (decomp).

1-(m-flurophenylaminocarbonyl)-1,2,3,9-tetrahydropyridino[2'3':3,4]-pyrrolo[1,2-b]-pyridazin-9-one may be prepared analogously m.p. 157°–16°.

1-(m-chlorophenylaminocarbonyl)-1,2,3,9-tetrahydropyridino[2'3':3,4]-pyrrolo[1,2-b]pyridazin-9-one may be prepared analogously m.p. 153°–160°.

What is claimed is:

1. A compound of the formula

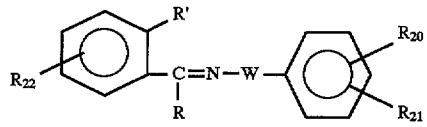

wherein

R' is a carboxyl group in a free acid, salt or ester form, a thiocarboxyl group in free acid or ester form, or a carbamoyl group;

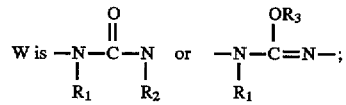

R and R$_1$ taken together form 2 to 4 membered alkylene, alkenylene or mixed alkylenealkenylene bridge which may bear one or more substituents selected from halogen, C$_{1-4}$alkyl, C$_{1-4}$alkoxy or phenyl optionally substituted with halogen, C$_{1-4}$alkyl, C$_{1-4}$haloalkyl or C$_{1-4}$alkoxy, and in which any methylene may be replaced by a group selected from oxygen, sulfur, NR$_{12}$, carbonyl or thiocarbonyl;

R$_2$ and R$_3$ are each independently hydrogen, C$_{1-4}$alkyl, C$_{1-4}$alkoxy, C$_{1-4}$alkylamino, C$_{1-4}$alkoxyC$_{1-4}$alkyl, or hydroxyC$_{1-4}$alkyl;

R$_{20}$, R$_{21}$ and R$_{22}$ are each independently hydrogen, halogen, C$_{1-4}$alkyl, C$_{2-4}$alkenyl, C$_{2-4}$alkynyl, C$_{1-4}$alkoxy, C$_{2-4}$alkenyloxy, C$_{2-4}$alkynyloxy, or C$_{1-4}$alkylthio each optionally substituted by 1 to 4 halogen atoms; phenyl or phenoxy each optionally substituted with nitro, cyano, hydroxy, amino, alkylamino, dialkylamino, alkylcarbonyl or alkoxycarbonyl; and R$_{12}$ is hydrogen, alkyl or alkoxy.

2. A compound according to claim 1 wherein R and R$_1$ taken together form 2 to 4 membered alkylene, alkenylene or mixed alkylenealkenylene bridge which may bear one or more substituents from halogen, C$_{1-4}$alkyl and C$_{1-4}$alkoxy.

3. A compound according to claim 2 wherein R$_{20}$, R$_{21}$ and R$_{22}$ are each independently hydrogen, halogen, C$_{1-4}$alkyl, C$_{1-4}$alkenyl, C$_{1-4}$alkynyl, C$_{1-4}$alkoxy, C$_{2-4}$alkenyloxy, $C_{2-4}$alkynyloxy, or $C_{1-4}$alkylthio each optionally substituted by 1 to 4 halogen atoms.

4. A compound according to claim 3 wherein R' is a carboxyl group in free acid or salt form.

5. A compound according to claim 4 wherein R and $R_1$ taken together are —$(CH_2)_2$—, —CH=CH— or —$(CH_2)_3$—.

6. A compound according to claim 5 wherein $R_{20}$ and $R_{21}$ are each independently hydrogen, halogen, $C_{1-4}$alkyl, $C_{1-4}$alkoxy and $C_{1-4}$haloalkyl.

7. A compound according to claim 6 wherein $R_{22}$ is hydrogen or halogen.

8. A compound according to claim 7 wherein W is

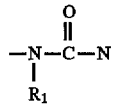

9. A compound according to claim 8 wherein $R_6$ is H or sodium cation; $R_{22}$ is hydrogen, fluoro, or chloro; R and $R_1$ taken together are —$(CH_2)_2$— or —$(CH_2)_3$—; $R_{20}$ is hydrogen, fluoro, chloro, methyl, ethyl, methoxy or trifluoromethyl; and $R_{21}$ is hydrogen, fluoro or chloro.

10. A compound according to claim 3 wherein $R_{22}$ is fluoro.

11. A method of controlling weeds or regulating plant growth which comprises applying to said weed or plant or the locus thereof a herbicidally plant growth regulating effective amount of a compound according to claim 1.

12. A herbicidal or plant growth regulating composition comprising a herbicidally or plant growth regulating effective amount of a compound according to claim 1.

* * * * *